(12) United States Patent
Eckermann et al.

(10) Patent No.: US 7,294,502 B2
(45) Date of Patent: Nov. 13, 2007

(54) DEVICE FOR COLLECTING LIQUID SAMPLES

(75) Inventors: Martin Eckermann, Rostock (DE);
Martin Ullmann, Hamburg (DE);
Bernd Lindner, Ratekau (DE)

(73) Assignee: EnviteC-Wismar GmbH, Wismar (DE)

( * ) Notice: Subject to any disclaimer, the term of this patent is extended or adjusted under 35 U.S.C. 154(b) by 484 days.

(21) Appl. No.: 10/479,049

(22) PCT Filed: May 28, 2002

(86) PCT No.: PCT/EP02/05868

§ 371 (c)(1),
(2), (4) Date: Feb. 18, 2004

(87) PCT Pub. No.: WO02/097389

PCT Pub. Date: Dec. 5, 2002

(65) Prior Publication Data

US 2004/0171173 A1     Sep. 2, 2004

(30) Foreign Application Priority Data

May 31, 2001   (DE) .............................. 101 26 583

(51) Int. Cl.
*G01N 33/53*      (2006.01)
(52) U.S. Cl. .................. 435/287.1; 436/518; 436/514; 436/527; 436/808; 436/810; 436/46; 436/165; 435/5; 435/6; 435/7.1; 435/7.2; 435/7.92; 435/805; 435/970; 435/287.2; 422/56; 422/58

(58) Field of Classification Search ................ 436/518, 436/514, 527, 808, 810, 46, 165; 435/5, 435/6, 7.1, 7.2, 805, 7.92, 970, 287.1, 287.2, 435/287.8; 422/56, 58
See application file for complete search history.

(56) References Cited

U.S. PATENT DOCUMENTS

| 2,905,169 | A |   | 9/1959  | Nieburgs |         |
|-----------|---|---|---------|----------|---------|
| 2,987,174 | A |   | 6/1961  | Free et al. |      |
| 5,441,698 | A |   | 8/1995  | Norell    |        |
| 5,468,648 | A | * | 11/1995 | Chandler | ..................... 436/518 |
| 5,648,274 | A | * | 7/1997  | Chandler | ..................... 436/514 |

(Continued)

FOREIGN PATENT DOCUMENTS

WO       WO 00/15020       3/2000

OTHER PUBLICATIONS

International Search Report for PCT Application No. PCT/EP02/05868, issued by the European Patent Office on Apr. 1, 2003.

*Primary Examiner*—Bao-Thuy L. Nguyen
(74) *Attorney, Agent, or Firm*—Reed Smith LLP; Stanley P. Fisher, Esq.; Juan Carlos A. Marquez, Esq.

(57) ABSTRACT

The invention relates to a device for collecting samples of fluids, in particular of body fluids such as saliva, said device comprising an absorbent pad and two housing parts which are connected to the latter in a movable manner and can enclose the absorbent pad. The device permits easy and safe handling when taking a sample and when transferring the sample for testing for an analyte in the sample. The device can also be handled hygienically and safely by persons not trained in taking samples.

15 Claims, 7 Drawing Sheets

U.S. PATENT DOCUMENTS 5,714,341 A * 2/1998 Thieme et al. ................ 435/22
5,726,010 A * 3/1998 Clark ............................. 435/5
5,900,379 A * 5/1999 Noda et al. ................. 436/518
5,922,614 A    7/1999 Cesarczyk
6,087,184 A * 7/2000 Magginetti et al. ......... 436/514
6,140,136 A * 10/2000 Lee ............................ 436/518
6,372,514 B1 * 4/2002 Lee ............................ 436/518
6,372,516 B1 * 4/2002 Sun ............................ 436/518
6,528,321 B1 * 3/2003 Fitzgerald et al. .......... 436/514

* cited by examiner

DEVICE FOR COLLECTING LIQUID SAMPLES

FIELD OF INVENTION

The present invention relates to a device for collecting samples of fluids, in particular of body fluids such as saliva.

BACKGROUND OF THE INVENTION

Body fluids are useful for detecting substances of diagnostic interest. These substances may be present at relatively high concentrations in the blood for example, so that they can easily be detected there. Other substances accumulate in the urine, which additionally has the advantage that it is easier to collect for analysis purposes. Moreover, many substances such as antibodies, antigens, pharmaceutical active substances and naturally occurring hormones, and also drugs, for example cocaine, can be detected in saliva. For detecting the relevant substances, a number of quick tests have been developed which in many cases are based on a single test strip through which the sample of fluid moves and, in the presence of a substance to be detected, triggers a color reaction for example.

Various devices for collecting samples of suitable fluids are known. In the simplest case, a test strip can for example be brought into direct contact with the sample of fluid, or, as is described in DE 198 30 405 A1, the test strip can be provided with a flexurally stiff holder for the test strip in order to protect said test strip from mechanical stresses. However, corresponding devices are in most cases not suitable for collecting saliva for example, the reason being that, in order to avoid direct contact with the analysis reagents in the test strip, they cannot be placed directly in the mouth. In addition, an undefined amount of sample is taken up by the test strip, so that fluctuations in the amount of sample taken up can lead to different measurement results.

A device for collecting saliva by means of an absorbent pad is disclosed in EP-A-0 418 739. This device comprises an absorbent pad which by means of a holder is introduced into the mouth. After the absorbent pad has taken up the saliva, it has to be stored in a separate container until such time as it is further tested. To do so, the absorbent pad can be separated from the holder by means of a special device. The device described for collecting saliva consists of several individual parts which have to be handled separately. In addition, there is a possibility that the person taking the sample will come into undesirable contact with the saliva sample from the person being tested or will inadvertently contaminate the sample. Finally, it is difficult for the person taking the sample to know whether the absorbent pad has taken up a sufficient amount of saliva. This may be of particular importance if, as a result of drug consumption, the person being tested has a reduced flow of saliva or refuses to cooperate willingly with the person taking the sample.

To ensure that a sufficient amount of saliva has been taken up into the absorbent pad of a device for collecting saliva, U.S. Pat. No. 5,714,341 proposes providing the absorbent pad with a further absorbent part in the handle of the device, said further absorbent part containing an indicator substance. When the absorbent pad is saturated with saliva, the saliva also spreads into the additional absorbent part of the device and there transports a dye to a viewing window, by which means a sufficient saturation of the absorbent pad with saliva is displayed. However, this has the disadvantage that the person being tested may potentially come into contact with the dye. In addition, the disclosed device for collecting saliva requires a separate device for detecting the desired analyte, so that the person taking the sample may come into contact with the saliva of the person being tested and, as a whole, the test is awkward to manage.

U.S. Pat. No. 5,479,937 discloses a device for collecting saliva in which an absorbent pad is secured on the plunger of a syringe and the pad, saturated with saliva when removed from the mouth, is squeezed out by means of the plunger in a syringe body in order to obtain the saliva. U.S. Pat. No. 4,774,962 proposes using centrifugation to obtain the saliva collected in an absorbent pad placed in the mouth of the person being tested. According to U.S. Pat. No. 4,418,702, the saliva is to be squeezed out from a corresponding saliva-saturated pad by means of a special screw device.

The above-described devices for collecting saliva have the disadvantage that they consist of a plurality of individual parts. This makes handling difficult especially for routine tests. In addition, having to handle a plurality of individual parts means that the person taking the sample can easily come into contact with the saliva-saturated pad. This is undesirable from the point of view of the person taking the sample and compromises the acceptance of corresponding routine tests, for example by the police. In addition, the complicated handling may lead to undesired contamination of the sample. Finally, with the known devices, it is difficult to obtain an easily reproducible amount of saliva and make this available for a subsequent test.

It is therefore an object of the present invention to make available a device for collecting samples of fluids, in particular of body fluids such as saliva, which permits safe, simple and hygienic handling even by untrained persons. In addition, there should be little chance of the person taking the sample coming into contact with the sample of fluid which has been taken up. The device is also intended to permit a quick test for a desired analyte without a plurality of individual parts having to be handled separately from one another. The sample should be collected and made available for the test in an amount that is as reproducible as possible. Finally, checking whether enough sample material has been taken up by the device should be easy to do, even when an untrained person is taking the sample.

SUMMARY OF THE INVENTION

It has now been found that this object is achieved by a device for collecting samples of fluids in accordance with the features of claim 1. The present invention thus concerns a device for collecting samples of fluids, said device comprising an absorbent pad and two housing parts which are connected to the absorbent pad in a movable manner, said housing parts being arranged in such a way that, in a first position of the housing parts, the absorbent pad can take up the sample of fluid, and, in a second position, the housing parts surround the absorbent pad.

The device according to the invention is suitable in particular for collecting body fluids and preferably for collecting saliva.

The device according to the invention comprises an absorbent pad and two housing parts which are connected to the absorbent pad in a movable manner. This movable connection is configured in such a way that, in a first position, the two housing parts expose the absorbent pad, i.e. do not surround it, so that it is accessible from outside at at least one point, but preferably completely, and can take up, i.e. absorb, the sample of fluid. In this first position, the two housing parts can, for example, have the function of a handpiece via which the device can be held while the absorbent pad is placed in the mouth so that it becomes absorbed with saliva.

The movable connection between the absorbent pad and the two housing parts is additionally configured in such a way that the two housing parts can be moved from the above-described first position to a second position in which they surround the absorbent pad and thus serve as a housing for the absorbent pad. The absorbent pad ought to be enclosed as far as possible completely by the housing parts, preferably in such a way that the sample of fluid located in the absorbent pad cannot escape from the housing thus formed.

In a preferred embodiment of the device according to the invention, the two housing parts are connected to the absorbent pad via at least one hinge. This hinge is preferably configured in such a way that the two housing parts can be connected to one another pivotably at at least one point and are connected to the absorbent pad, said absorbent pad being located between the two housing parts. This allows the two housing parts to pivot open into their first position, with the absorbent pad thus being exposed. When the two housing parts are pivoted shut, they move into their second position in which they surround the absorbent pad.

The absorbent pad can be connected directly to the two housing parts. However, the absorbent pad is advantageously secured on a holder on which the housing parts are articulated. In this way, in the first position of the housing parts, i.e. when the device has been pivoted open, a distance is defined between the housing parts, serving for example as a handpiece, and the absorbent pad, so that the absorbent pad can be more easily placed in the mouth.

The hinge situated between the housing parts and permitting a movement of the housing parts between the first and second positions can in principle be any hinge which permits a desired movement of the housing parts, for example a hinge with a pin which joins the two housing parts and the absorbent pad and holder together. Alternatively, for example, a kink can be provided between the two housing parts, for example in the form of a narrowing of the wall thickness. This narrowing can be obtained for example during the injection-molding of the device, by which means at least the two housing parts can be obtained in one piece in one work step.

The absorbent pad can be made of any material suitable for absorbing a sample of the desired fluid. It can for example be a sponge, pressed cotton or cellulose, or a thick piece of absorbent paper. The absorbent pad is preferably made of pressed cellulose. This has the advantage that a strip of pressed cellulose is flat in the dry state and, when wet, swells out two to three times compared to the dry state. This means that even an untrained user can tell whether the absorbent pad has been sufficiently soaked with the sample of fluid, especially if the absorbent pad is approximately as thick as the holder in the dry state for example. Then the swelling of the pad can be observed particularly easily. In addition, pressed cellulose takes up a well defined amount of fluid, so that the amount of sample to be taken up with the device according to the invention can be determined relatively precisely by means of the extent of the absorbent pad.

Alternatively, the absorbent pad can be made of another material suitable for collecting or taking samples, for example a flow material, e.g. of polyolefin. However, such a material may not have the property of increasing in volume and thus indicating the amount of sample taken up. As an indication that a sufficient amount of sample has been taken up, it is also possible to use, for example, surface effects in the holder of the absorbent pad. For this purpose, the absorbent pad can advantageously be guided underneath a transparent and roughened surface of the holder. A corresponding surface is opaque in the dry state and becomes clear upon contact with fluid, so that if the corresponding portion of the holder becomes clear this indicates that a sufficient amount of sample has been taken up by the absorbent pad. Alternatively, a dye indicator can be used, for example as is described in U.S. Pat. No. 5,714,341, to indicate that a sufficient amount of sample has been taken up.

A suitable material for the absorbent pad can easily be chosen by the person skilled in the art. Pressed cellulose is preferred in particular if the device according to the invention is intended to be used for collecting saliva from the oral cavity. Other materials may be necessary if the analyte to be detected is incompatible with pressed cellulose, for example because of nonspecific absorption, etc.

The amount of the sample of fluid to be collected with the device according to the invention is preferably between 25 and 500 µl, in particular between 200 and 400 µl, for example ca. 300 µl. A range of 80 to 250 µl is also advantageous, e.g. 125 µl. To guarantee reproducible test results, the error tolerance should be ca. ±10-20 µl. This can be achieved for example with an absorbent pad made of pressed cellulose which in the dry state is about 1 cm long, 6 mm wide and 1.5 to 2 mm thick. However, the size of the absorbent pad is finally dependent on the pore size and type of material and can be chosen by the skilled person to suit the desired purpose.

The absorbent pad can additionally comprise a means stimulating the flow of saliva. Examples of means stimulating the flow of saliva are citric acid or flavoring agents. A design of the device according to the invention with a means for stimulating the flow of saliva is of advantage particularly if a sample of saliva is to be taken from persons with reduced saliva flow. A reduced saliva flow may occur for example in individuals who have taken certain drugs. The design of the device according to the invention with a means for stimulating the flow of saliva is therefore advantageous particularly if the device is to be used for detecting drugs in the saliva of the persons being tested.

The absorbent pad can be connected to the two housing parts directly or via a holder. The connection between the absorbent pad and the two housing parts or holder can in principle be formed in any desired way. For example, the absorbent pad can be adhesively bonded to the holder, or the holder can be cast onto the absorbent pad in one step directly during injection-molding. In a further embodiment, the absorbent pad can be inserted into a recess provided for this purpose in the holder, said recess then preferably having an arrangement, such as inwardly pointing teeth, preventing the absorbent pad from being withdrawn from the recess.

In a particularly advantageous embodiment, the device according to the invention comprises not only the above-described individual parts for collecting a sample of fluid, but also a means for detection of at least one analyte to be detected in the sample of fluid. The analytes to be detected may be very different depending on the nature of the sample collected. If the sample is a body fluid, it may for example be desirable to detect certain hormones, antibodies, pharmaceutical substances and/or drugs as analytes in the sample.

The means for detection of at least one analyte in the sample of fluid advantageously comprises one or more test strips (e.g. immunochromatographic test strip/lateral flow immunoassay), where each test strip may be suitable for the detection of one or more analytes. Corresponding test strips for a wide variety of analytes are known to the skilled person and can be combined with the device according to the invention. For example, the device according to the invention can contain 1, 2, 3, 4 or 5 test strips, the number of test strips depending only on their size, the size of the device according to the invention, and the amount of the sample needed for each test strip and available in the absorbent pad. In general, the sample volume or the size of the device is chosen such that the desired number of test strips is realizable. If the device comprises a plurality of test strips, these are preferably arranged parallel to one another.

Suitable test strips normally have an application zone onto which the sample of fluid to be examined is applied. The sample moves from there into a reaction zone in which the analyte to be detected triggers a color reaction, for example. The appearance of a color change in the reaction zone then indicates the presence of an analyte to be detected in the sample. Alternatively, depending on the nature of the test strip, it may be that no color change, or only a slight color change, indicates a positive test result.

To make handling of the device according to the invention as simple as possible, and in particular to ensure that the person taking the sample does not have to manipulate or even touch the pad saturated with the sample in order to bring the sample into contact with the detection system for the analyte to be detected, the device according to the invention can comprise a squeezing arrangement which, when the housing parts are moved into their second position in which they surround the absorbent pad, squeezes the fluid out of the latter.

The squeezing arrangement can for example be a raised part in one or both of the housing parts which, when the two housing parts are moved into their second position in which they surround the absorbent pad, presses on the absorbent pad and squeezes the fluid out. Advantageously, the second housing part comprises an area matching the raised area in the first housing part, so that the pressure exerted by the raised area not only presses the absorbent pad away from it but also presses on the matching area in the second housing part and thus squeezes the fluid out. This means that, upon closing of the housing parts, the sample collected in the absorbent pad is automatically squeezed out of the pad and made available for further analysis. Special handling or touching by the person taking the sample is not needed. The person taking the sample can easily and safely close the device according to the invention and at the same time make the collected sample available for further analysis without coming into contact with the sample.

To permit automatic application of the sample onto the test strip or test strips, these should be arranged in one of the housing parts in such a way that, when the housing parts are moved into their second position in which they surround the absorbent pad, the squeezing arrangement squeezes the sample of fluid out of the absorbent pad onto the application zone of the test strips. In this way, when the housing is closed, the sample is automatically applied at the correct place and in the correct amount to the application zone of the test strips, so that reproducible test results are ensured.

When the housing is open, i.e. when the housing parts are located in their first position, then, in order to ensure that the test strip or test strips cannot be inadvertently touched or contaminated, the test strips are preferably arranged in one of the housing parts between the housing wall and a dividing wall. This dividing wall can have an inlet opening through which the sample of fluid when squeezed out of the absorbent pad can reach the test strips during closure of the housing. This inlet opening can for example comprise one or more holes in the dividing wall. Alternatively, the dividing wall can also have a larger opening which then preferably contains a grating or a porous body against which the absorbent pad can be pressed, upon closure of the housing, in order to squeeze the sample out of the absorbent pad. The holes in the dividing wall, grating or porous body should be so dimensioned that the sample can easily pass through them. In the case of a sample with low viscosity, the holes can be relatively small. In the case of a more viscous sample, for example saliva, the holes should be correspondingly bigger.

In a further embodiment, one of the housing parts of the device according to the invention comprises a storage chamber for a liquid. This storage chamber can be arranged in such a way that, when the housing parts are moved into their second position, i.e. upon closure of the housing, it is situated on one side of the absorbent pad, and the application zone of the test strips on the other side of the absorbent pad. The storage chamber can thus act for example as a squeezing arrangement and can at the same time squeeze the sample out of the pad and additionally emit a liquid which contributes to washing out the pad and increases the amount of fluid available for the subsequent test. The liquid in the storage chamber can for example be a solution such as a buffer solution which stabilizes the analyte present in the sample or in some other way assists the subsequent test.

The storage chamber can for example be designed as a sponge which, upon closure of the housing, presses against the absorbent pad and thus releases the fluid contained in the sponge. Advantageously, the storage chamber can also be for example a closed chamber which is provided for example with a blister seal. In this way, it is possible to ensure that the fluid does not escape too early or to ensure that the pad does not completely dry out. Upon closure of the housing, the blister seal can for example be automatically opened by a suitable device, for example a needle or a pointed tip, so that the liquid can escape from the storage chamber.

If the device according to the invention is equipped with at least one test strip for detection of at least one analyte in the sample of fluid, it preferably comprises a viewing window through which the test strip or test strips can be observed. This means that the test result, for example indicated by a color change in the reaction zone of the test strips, can be read off without again opening the housing. To do this, the test strips should be arranged alongside one another in such a way that they can be observed simultaneously through the viewing window. The viewing window can be a cutout in one of the housing parts. However, this has the disadvantage that, when the two housing parts have been moved into their second position, the housing is not completely closed, and instead residual fluid can escape. The viewing window is therefore preferably sealed off with a transparent material such as a glass panel or a clear film. This also has the advantage that, if the test strip or tests strips is/are to be read off automatically by means of an optical reading system, it improves the reflective properties of the test strips, which in many cases are made of nitrocellulose and therefore lead to diffuse light scattering. In addition, a transparent material between the test strips and the optical reading system prevents steaming up of the optical reading system, even if a relatively large sample volume was applied onto the test strips and these are therefore moist.

The viewing window can be provided in the housing part in which the test strip or test strips is/are also located. Alternatively, the viewing window can be situated in the housing part lying opposite the housing part with the test strip or test strips. In this case, it is necessary, for example by providing additional cutouts in the dividing wall below which the test strip or test strips is/are located, and in the holder for the absorbent pad, to ensure that the reaction zone of the test strips can be observed through the viewing window. If several cutouts are provided, a transparent material can be used to seal off none, several or all of these cutouts. Moreover, at least one test strip can be located in the housing part which comprises the viewing window, and at least one further test strip can be located in the other housing part, which may if appropriate be provided with a second viewing window.

The size of the viewing window is of no particular importance, but it should be such that at least the reaction zone of the test strip or test strips can be observed. Alternatively, it is also possible for one or both of the housing parts or the whole device according to the invention to be made of a transparent material. In this case, it is possible to do without a viewing window for observing the test strip or test strips.

The housing and the arrangement for holding the absorbent pad can in principle be made of any desired materials. They are preferably made of plastic, for example polypropylene or polyethylene, which is brought to the desired shape by injection-molding for example.

In a further preferred embodiment, the device according to the invention is configured in such a way that a lower housing part is first pivoted under the absorbent pad and only then the upper housing part is pivoted over the absorbent pad in order to close the housing. This further facilitates the handling of the device according to the invention and ensures that the person taking the sample does not come into contact with the sample in the absorbent pad. This permits completely hygienic handling of the device according to the invention and increases the acceptance in the case of untrained users, for example policemen during routine checks, for example for drug abuse.

The device according to the invention is also suitable as a disposable test in which a sample is first taken and then enclosed directly in the device, without excess solution being able to escape or without subsequent manipulation of the test. This permits safe storage of the test sample while at the same time allowing the test result to be read off. To prevent possible manipulation of the test sample, the device according to the invention can additionally contain an indicator arrangement which indicates that the housing has been opened after the housing parts have been moved into their second position, in which they enclose the absorbent pad. Such an indicator arrangement can be for example a snap-fit closure piece which, after it has been locked, can only be opened again by breaking it.

BRIEF DESCRIPTION OF THE DRAWINGS

The device according to the invention is now described in more detail with reference to the attached figures which show a preferred illustrative embodiment, but without limiting the invention to this embodiment. In the attached figures.

DETAILED DESCRIPTION OF THE INVENTION

Figure 1:
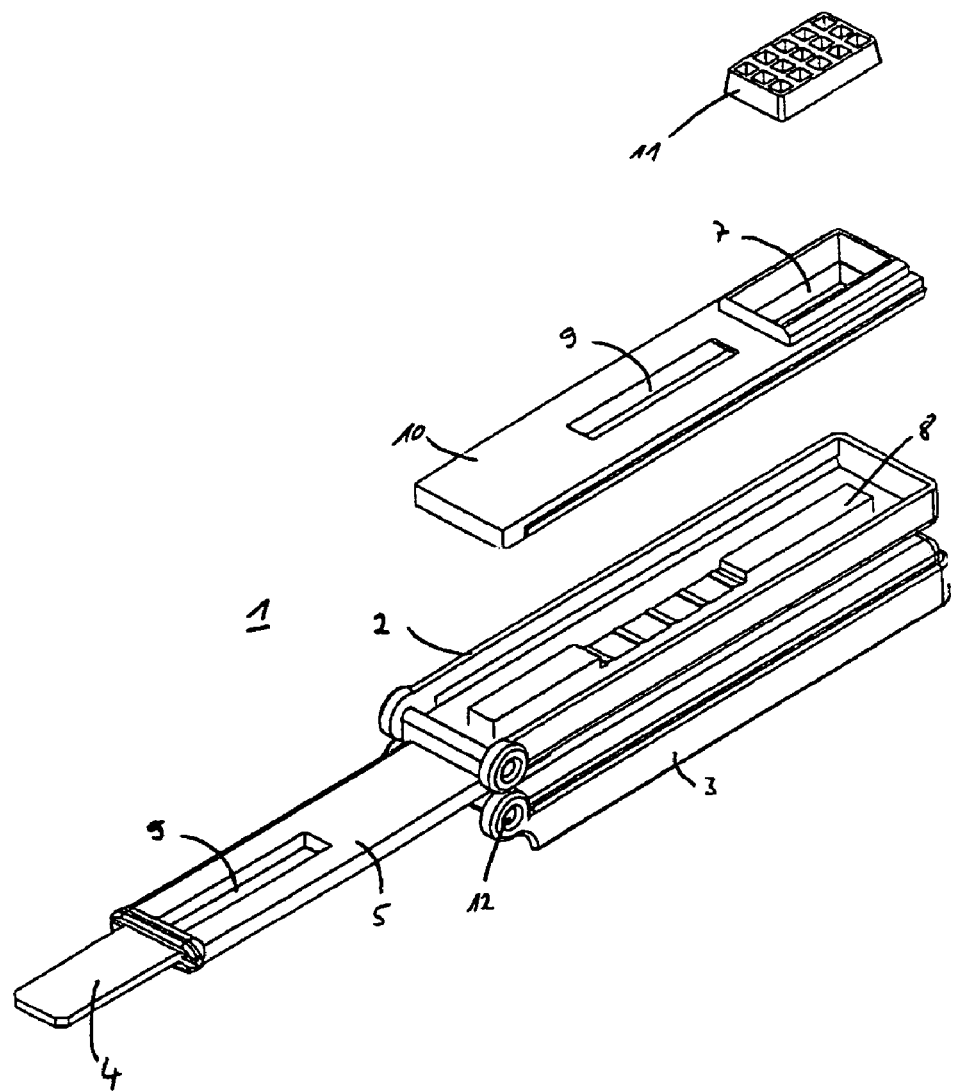
FIG. 1 shows an exploded view of the device according to the invention, in a perspective representation from underneath, with the housing opened.

In FIG. 1, a preferred embodiment of the device 1 according to the invention is depicted in an exploded perspective view. The absorbent pad 4 is secured on a holder 5 which is connected to the lower part 2 of the housing and to the upper part 3 of the housing. The two housing parts are connected to one another via the hinges 12 and can be pivoted via the hinges 12 from the illustrated first position, in which the absorbent pad 4 can take up a sample of fluid, to a second position in which they surround the absorbent pad 4. The housing part 2 comprises a test strip 8 located between the wall of the housing part 2 and the dividing wall 10. The dividing wall 10 has an inlet opening 7 provided with a grating 11. When the housing is closed, the absorbent pad 4 is pressed, by means of squeezing arrangement 6 (not shown in FIG. 1) in the housing upper part 3, against the grating 11 so that a sample of fluid taken up previously in the pad 4 passes through the grating 11 to the test strip 8. The dividing wall 10, the holder 5 and (not shown in FIG. 1) the housing upper part 3 have viewing windows 9 through which the test strip 8 can be observed.

When the device according to the invention shown in FIG. 1 is used to collect a sample of saliva, for example, the absorbent pad 4 on the holder 5 is placed in the mouth of the person being tested and kept there until the absorbent pad 4 is soaked with the saliva of said person being tested. A period of about half a minute is generally sufficient for this, although this period depends on the absorbency and size of the pad 4 and on the presence of saliva and the flow of saliva. The absorbent pad 4 should preferably take up ca. 200-400 µl, in particular about 300 µl of saliva. For example, an absorbent pad 4 made of pressed cellulose and measuring about 1 cm in length, 6 mm in width and 1.5 to 2 mm in thickness would be suitable for this purpose. After the absorbent pad 4 has been soaked with the saliva of the person being tested, the device according to the invention can be taken hold of at housing parts 2 and 3 by the person collecting the sample, without said person coming into contact with the saliva-saturated absorbent pad 4. One of the housing parts is then preferably pivoted so that it comes to lie under the absorbent pad 4 and the holder 5. Then the other housing part is likewise pivoted so that the absorbent pad 4 and the holder 5 are enclosed between the two housing parts 2 and 3. Alternatively, both housing parts 2 and 3 can be pivoted simultaneously.

Figure 2:
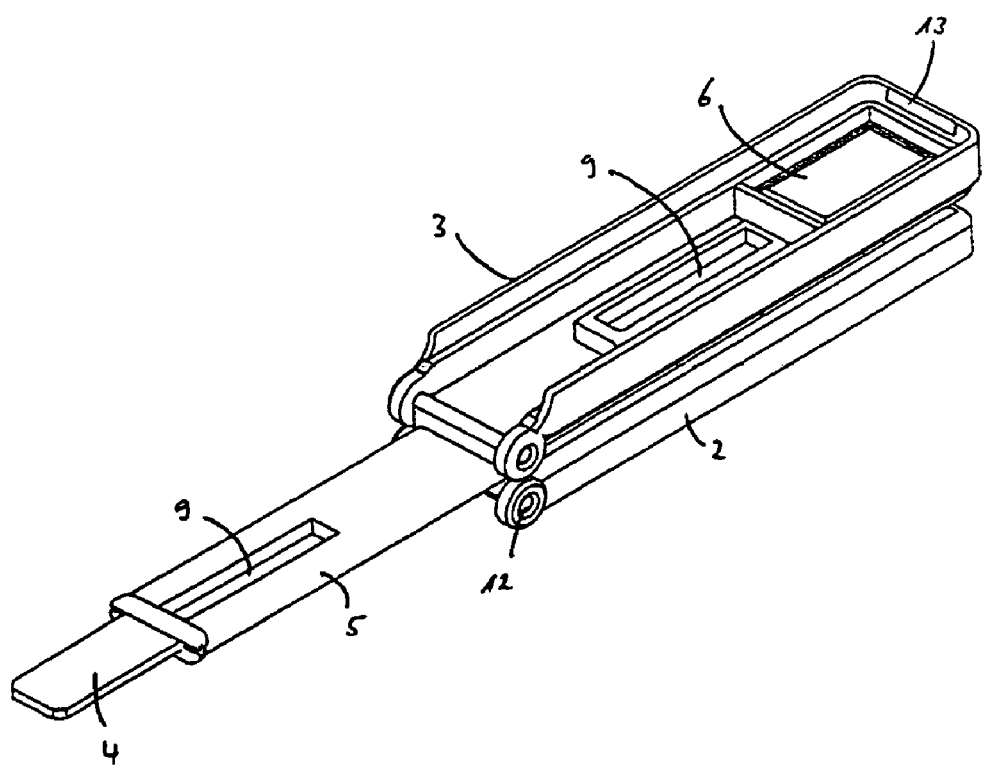
FIG. 2 shows a perspective view, from above, of the device according to the invention when open.

When the two housing parts 2 and 3 are closed, the saliva-saturated absorbent pad 4 is pressed, by means of a squeezing arrangement 6 shown in FIG. 2 on the housing upper part 3, against the grating 11 in the inlet opening 7 of the dividing wall 10, as a result of which the saliva is transferred from the absorbent pad 4 through the grating 11 and onto the test strip 8. From the application zone of the test strip 8, the saliva migrates into the reaction zone of the test strip where, if a specific analyte, for example a drug, is present in it, it triggers a color change. This color change of the test strip can be observed through the viewing windows 9, without the housing having to be opened. The squeezing arrangement 6 can additionally or alternatively be a storage chamber for a liquid.

In FIG. 2, a snap-fit closure piece 13 is also shown on the upper part 3 of the housing, which snap-fit closure piece 13 engages in a corresponding recess in the bottom part 2 of the housing when said housing is closed. In this way, renewed opening of the housing is prevented.

Figure 3:
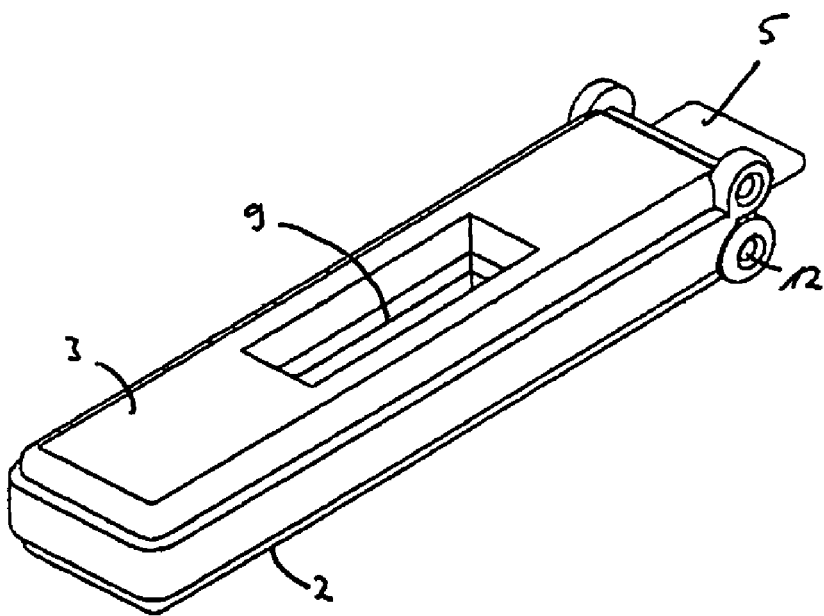
FIG. 3 shows a perspective view, from above, of the device according to the invention when closed.

FIG. 3 shows a perspective view of the device according to the invention shown in FIGS. 1 and 2, here with the device closed. The figure shows the housing parts 2 and 3 which are connected to one another via the hinges 12, and the viewing windows 9 through which the test strip (not visible here) can be observed.

Figure 4:
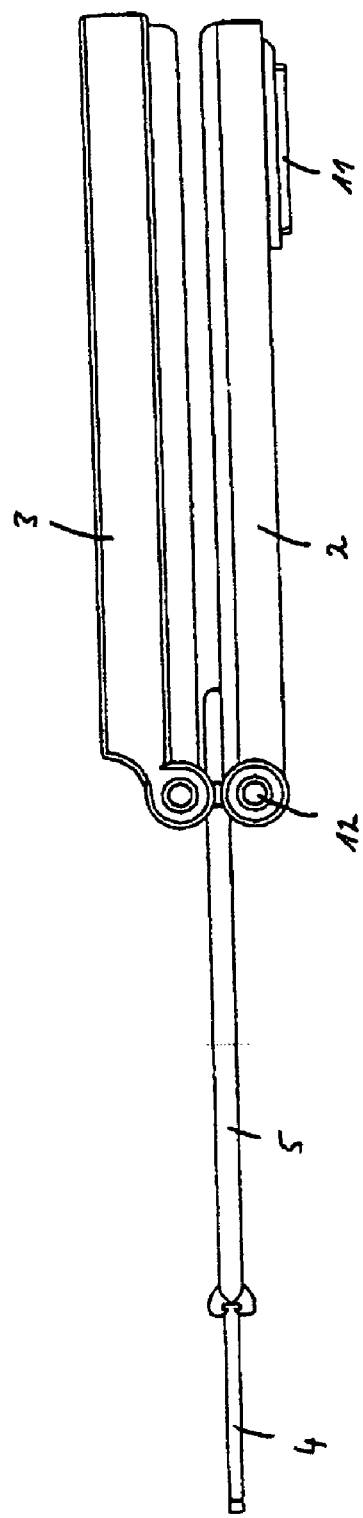
FIG. 4 shows a side view of the device according to the invention when open.

FIG. 4 shows a side view of the device according to the invention, with the housing opened. Protruding from the lower part 2 of the housing is the grating 11 against which the absorbent pad 4 is pressed by the lower part 3 of the housing when the two housing parts are closed.

Figure 5:
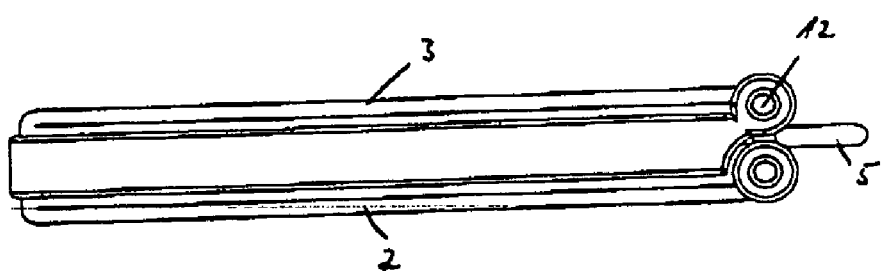
FIG. 5 shows a side view of the device according to the invention when closed.

FIG. 5 shows the same device as in FIG. 4, but when closed.

Figure 6:
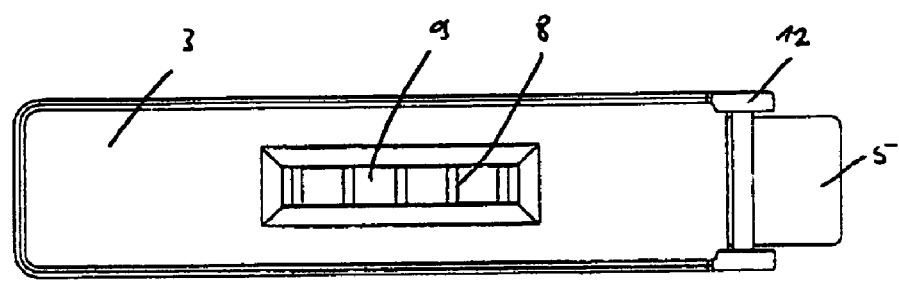
FIG. 6 shows a view, from above, of the device according to the invention when closed.

FIG. 6 shows the device according to the invention from above. The figure indicates the upper part 3 of the housing with the viewing window 9 through which the test strip 8 can be viewed.

Figure 7:
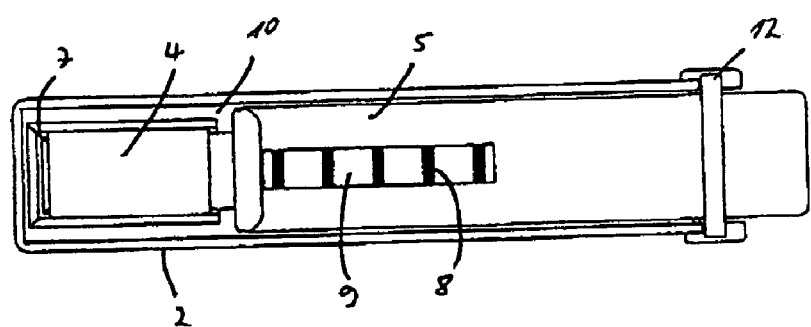
FIG. 7 shows a view, from above, of the device according to the invention when closed, but without the upper housing part.

FIG. 7 shows the same device as in FIG. 6, but without the upper part 3 of the housing. The figure indicates the absorbent pad 4 with holder 5 lying on the dividing wall 10 of the lower part 2 of the housing. The absorbent pad 4 is located over the inlet opening 7. In the holder 5 there is a viewing window 9 through which the test strip 8 can be observed.

The invention claimed is:

1. A device for collecting samples of fluids, said device comprising:
    a) a housing comprising an upper part and a lower part;
    b) an absorbent pad secured to a holder;
    wherein, the upper and lower parts of the housing are pivotally connected to the holder such that in a first position of the housing, the absorbent pad is exposed to take up the sample fluid, and in a second position of the housing, the upper and lower parts surround the holder and the absorbent pad.

2. The device as claimed in claim 1, which device is adapted for collecting body fluids.

3. The device as claimed in claim 2, which device is adapted for collecting saliva from the oral cavity.

4. The device as claimed in claim 1, in which the lower and upper parts are connected to the holder via at least one hinge.

5. The device as claimed in claim 1, in which the absorbent pad comprises pressed cellulose.

6. The device as claimed in claim 1, in which the absorbent pad comprises a means for stimulating the flow of saliva.

7. The device as claimed in claim 1, comprising at least one test strip for detection of at least one analyte in the sample of fluid.

8. The device as claimed in claim 1, in which the housing parts comprise a squeezing arrangement which, when the lower and upper parts are moved into their position in which they surround the absorbent pad, squeezes the fluid out of the latter.

9. The device as claimed in claim 7, in which the test strip or test strips has/have an application zone for the sample of fluid, and the test strip or test strips is/are arranged in the housing in such a way that, when the lower and upper housing parts are moved into their second position in which they surround the absorbent pad, the squeezing arrangement squeezes the sample of fluid out of the absorbent pad onto the application zone of the test strip(s).

10. The device as claimed in claim 7, in which the test strip or test strips is/are arranged in one of the lower or upper housing parts between the housing wall and a dividing wall.

11. The device as claimed in claim 10, in which the dividing wall has an inlet opening through which the sample of fluid can pass to the test strip or test strips.

12. The device as claimed in claim 1, in which one of the lower or upper housing parts comprises a storage chamber for a liquid.

13. The device as claimed in claim 7, in which the device comprises at least one viewing window through which the test strip or test strips can be observed.

14. The device as claimed in claim 13, in which the viewing window is closed with a transparent material.

15. The device as claimed in claim 1, further comprising a means that indicates reopening of the housing.

* * * * *